US012805880B2

(12) United States Patent
Korman

(10) Patent No.: US 12,805,880 B2
(45) **Date of Patent: *Nov. 24, 2026**

(54) PREFERENTIAL REMOVAL OF CARTILAGE

(71) Applicant: WRIGHT MEDICAL TECHNOLOGY, INC., Memphis, TN (US)

(72) Inventor: Zachary Korman, Memphis, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 19/321,419

(22) Filed: Sep. 8, 2025

(65) Prior Publication Data

US 2026/0000420 A1 Jan. 1, 2026

Related U.S. Application Data

(63) Continuation of application No. 18/041,556, filed as application No. PCT/US2021/071091 on Aug. 4, 2021, now Pat. No. 12,426,908.

(60) Provisional application No. 63/106,457, filed on Oct. 28, 2020.

(51) Int. Cl.
*A61B 17/16* (2006.01)

(52) U.S. Cl.
CPC ................................ *A61B 17/1615* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1659; A61B 17/320016; A61B 17/32002; A61B 2017/564
See application file for complete search history.

(56) References Cited

U.S. PATENT DOCUMENTS

| | | | | |
|---|---|---|---|---|
| 5,759,185 A * | 6/1998 | Grinberg | A61B 17/1615 | 606/180 |
| 5,913,867 A * | 6/1999 | Dion | A61B 17/32002 | 606/180 |
| 6,258,093 B1 * | 7/2001 | Edwards | A61B 17/164 | 606/85 |
| 8,192,436 B2 * | 6/2012 | Schmitz | A61B 17/1671 | 606/85 |
| 8,460,298 B2 * | 6/2013 | O'Donoghue | A61B 17/1615 | 606/80 |
| 8,845,639 B2 * | 9/2014 | Wallace | A61B 17/1671 | 606/85 |
| 11,241,248 B2 * | 2/2022 | Behzadi | A61B 17/1659 | |
| 11,253,271 B2 * | 2/2022 | Kulas | A61B 17/1615 | |
| 11,883,056 B2 * | 1/2024 | Behzadi | A61B 17/142 | |
| 12,426,908 B2 * | 9/2025 | Korman | A61B 17/1615 | |
| 12,446,897 B2 * | 10/2025 | Korman | A61B 17/1615 | |

(Continued)

FOREIGN PATENT DOCUMENTS

WO WO-2022094499 A1 * 5/2022 ......... A61B 17/1615

*Primary Examiner* — Eric S Gibson
(74) *Attorney, Agent, or Firm* — DUANE MORRIS LLP

(57) ABSTRACT

Disclosed is a method for preferentially removing cartilage from a bone in a joint that is effective at removing the cartilage while minimizing any removal of the cortical bone.

12 Claims, 6 Drawing Sheets

(56) References Cited

U.S. PATENT DOCUMENTS

| | | | | |
|---|---|---|---|---|
| 2013/0006267 | A1* | 1/2013 | Odermatt | B25J 9/1628<br>901/41 |
| 2013/0011810 | A1* | 1/2013 | Cho | A61C 8/0089<br>433/165 |
| 2015/0057664 | A1* | 2/2015 | Scianamblo | B23B 51/02<br>606/80 |
| 2015/0150565 | A1* | 6/2015 | Huwais | A61C 8/0089<br>606/84 |
| 2017/0071704 | A1* | 3/2017 | Huwais | A61C 1/0061 |
| 2018/0078279 | A1* | 3/2018 | Germain | A61B 17/320758 |
| 2018/0263649 | A1* | 9/2018 | Germain | A61B 17/1633 |
| 2019/0029695 | A1* | 1/2019 | Huwais | A61B 17/1673 |
| 2019/0350726 | A1* | 11/2019 | Behzadi | A61F 2/4657 |
| 2019/0374246 | A1* | 12/2019 | Malkevich | A61B 17/32002 |
| 2020/0178998 | A1* | 6/2020 | Behzadi | A61B 17/1675 |
| 2021/0290346 | A1* | 9/2021 | Huwais | A61C 8/0089 |
| 2022/0117620 | A1* | 4/2022 | Behzadi | A61B 17/1659 |
| 2023/0098719 | A1* | 3/2023 | Korman | A61B 17/1615<br>408/230 |
| 2023/0301677 | A1* | 9/2023 | Korman | A61B 17/1615 |
| 2026/0000420 | A1* | 1/2026 | Korman | A61B 17/1615 |
| 2026/0020866 | A1* | 1/2026 | Korman | A61B 17/1615 |

* cited by examiner

PREFERENTIAL REMOVAL OF CARTILAGE

CROSS-REFERENCE TO RELATED APPLICATIONS

This application is a continuation filed under 37 C.F.R. § 1.53 claiming the benefit under 35 U.S.C. § 120 of any and all applications for which a foreign or domestic priority claim is identified in the Application Data Sheet as filed with the present application, including U.S. patent application Ser. No. 18/041,556, filed Feb. 14, 2023, which is a National Stage Application, filed under 35 U.S.C. 371, of International Patent Application No. PCT/US2021/071091, filed Aug. 4, 2021, which claims priority to U.S. Provisional Application No. 63/106,457, filed on Oct. 28, 2020, and are hereby incorporated by reference in accordance with 37 C.F.R. §§ 1.57; 1.97; and 1.98 in their entireties.

FIELD

The present disclosure relates to surgical procedures for removing cartilage material and more particularly to a procedure for preferentially removing cartilage material in a joint.

BACKGROUND

In surgical procedures such as arthrodesis the layer of cartilage on subchondral bone is removed using an arthroscopic burr. However, although it is desirable to completely remove the cartilage without removing the underlying subchondral bone, in practice the surgeons find is very difficult or impossible not to remove undesirable amount of the underlying subchondral bone during the cartilage removal procedure using arthroscopic burrs. The difficulty lies in the nature of the minimally invasive surgery (MIS) arthrodesis procedures where the surgeons are performing the cartilage removal procedure without the benefit of visual confirmation.

The above-mentioned problem is attributed to the fact that the various burrs used surgical procedures are generally designed and optimized for removal of harder tissues such as cortical bone and because their cutting action is so effective, when surgeons are using the conventional burrs for removing cartilage, which is softer than cortical bone, the surgeons do not realize when the burr has gone completely through the cartilage and the burr is starting to cut into the subchondral bone. Because visual observation of the joint surfaces is not common practice for MIS arthrodesis procedures, the surgeons often have to rely on tactile feedback when performing the cartilage removal. The effectiveness of the burr's cutting action, however, provides no tactile feedback to the surgeon during the transition when the burr has cut through the cartilage and is beginning to cut the subchondral bone. For the very effective conventional burr, there is no noticeable difference in the resistance to cutting action presented by the cartilage vs. the subchondral bone.

Thus, there is a need for an improved method that for removing cartilage in a joint, especially for MIS procedures.

SUMMARY

Disclosed herein is an improved novel method for removing cartilage utilizing a particular combination of a burr having a rake angle in a specified range, a burr diameter in a specified range, and a particular rotational speed for the burr that unexpectedly resulted in effective removal of cartilage from bones while minimally abrading the underlying cortical bone. The disclosed method is particularly useful in MIS procedures.

Provided is a method for preferentially removing cartilage from a bone in a joint comprising: inserting a burr into a joint comprised of cartilage attached to subchondral bone; and maneuvering the burr within the joint against the cartilage while rotating the burr at a speed not more than about 10,000 revolutions per minute (rpm), wherein the burr comprises a plurality of cutting flutes that have a negative rake angle of −10 to −50 degrees, whereby the cartilage is preferentially removed from the subchondral bone and the rotating burr provides a tactile feedback to the operator when the rotating burr has gone through the cartilage and contacts the subchondral bone.

BRIEF DESCRIPTION OF THE DRAWINGS

The inventive concepts of the present disclosure will be described in more detail in conjunction with the following drawing figures. The structures in the drawing figures are illustrated schematically and are not intended to show actual dimensions.

DETAILED DESCRIPTION

Figure 1:
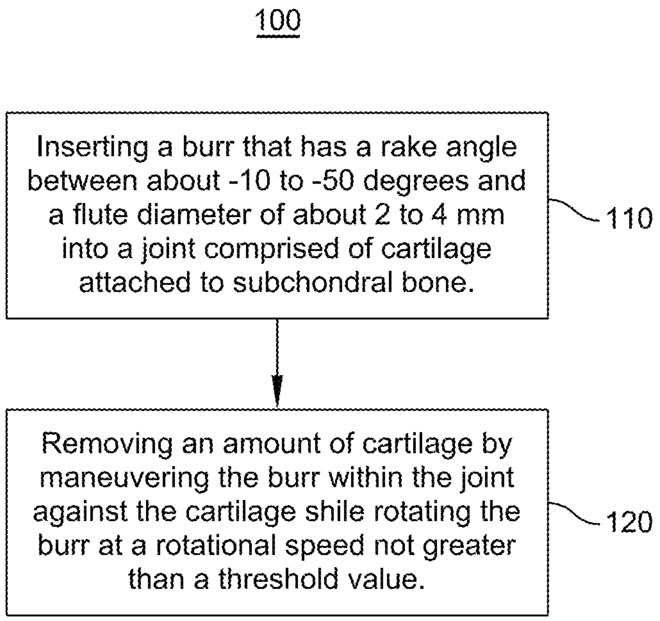
FIG. 1 is a flowchart illustrating the novel method of the present disclosure.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

Unless otherwise expressly stated, it is in no way intended that any method set forth herein be construed as requiring that its steps be performed in a specific order, nor that with any apparatus, specific orientations be required, unless specified as such. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

Provided herein is a method for preferentially removing cartilage from a bone in a joint using a burr whose cutting flutes have a negative rake angle that is within a specified range, a diameter that is within a specified range, at a rotational speed that is below a specified threshold value. FIG. 1 is a flowchart 100 illustrating the method according to the present disclosure. The method comprises inserting the burr having a rake angle between about −10 to −50 degrees and a diameter of about 2 to 4 mm into a joint comprised of cartilage attached to subchondral bone. See step 110. Then, removing an amount of cartilage by maneuvering the burr within the joint against the cartilage while rotating the burr at a rotational speed that is not greater than a maximum threshold speed of about 10,000 revolutions per minute (rpm). In preferable embodiments, the rotational speed of the burr should be greater than or equal to 0.5 rpm. See step 120. The rake angle of the burr is described below in connection with FIG. 2. As the cutting flute portion of the burr can have a variety of shapes (i.e. straight edged cylindrical shape, conical shape, bulbous shape having a maximum diameter in the middle, etc.), the diameter of the burr is measured as the maximum diameter of the fluted portion of the burr.

Figure 2:
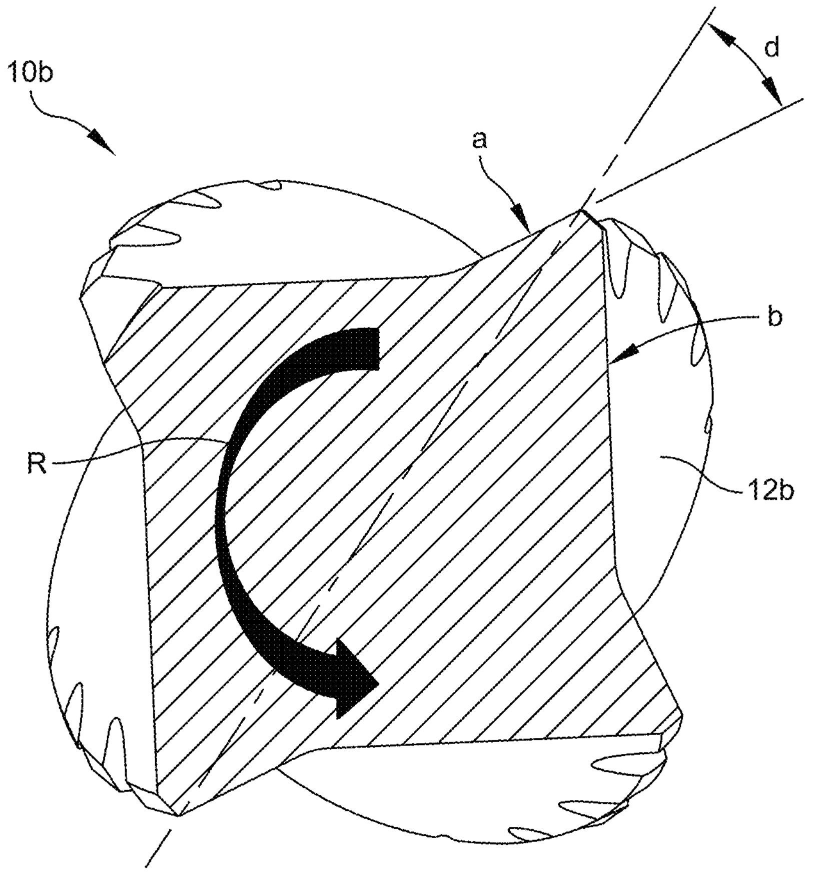
FIG. 2 is a cross-sectional view of the surgical burr of FIG. 3B taken along the section line A-A showing the perimeter of the cutting flutes and their negative rake angle.

FIG. 2 graphically explains the anatomy of an exemplary cutting flute 12*b* on the burr 10*b* and identifies the negative rake angle d of the cutting flute 12*b*. FIG. 2 is a schematic cross-sectional view of the burr 10*b* of FIG. 3B. In FIG. 2, the arrow R denotes the rotation direction for the burr 10*b* and "a" is a rake face, "b" is a clearance face, and "d" is the rake angle for the defined rotation direction R.

The inventors unexpectedly discovered that when the burr having the specified rake angle and diameter is used below the maximum threshold rotational speed, the burr is effective at removing cartilage tissue but not effective at cutting into the subchondral bone. Additionally, because the combination of the burr structure and the rotational speed is not effective at cutting into the subchondral bone, the operating surgeon receives a clear tactile feedback from the burr when the burr has gone through the cartilage and makes a contact with the underlying subchondral bone because the burr's cutting blades skid or slide over the surface of the subchondral bone. The surgeon can use this tactile feedback to reduce the pressure applied on the burr and to move to other parts of the surgical site to remove cartilage. Without being bound by any particular theory, it appears that when the method of the present disclosure is utilized, the cutting energy generated at the cutting edges of the burr's flutes is maintained below certain threshold level that is required to cut into the subchondral bone. This unexpected discovery is supported by the cadeveric test data presented herein.

In some embodiments, the burr can have a rake angle between about −20 to −40 degrees. In some embodiments, the rake angle is about −10±5 degrees (i.e., from −5 to −15 degrees). In some embodiments, the rake angle is about −20±5 degrees. In some embodiments, the rake angle is about −40±5 degrees. In some embodiments, the rake angle is about −50±5 degrees. In a preferred embodiment, the burr has a rake angle of at least −30±5 degrees and a diameter of about 3 mm. The use of the term "about" in connection with the dimensional parameters are meant to account for the variations that can be expected in typical manufacturing processes for surgical tools such as burrs.

In some embodiments, the maximum threshold rotational speed for the burr during the cartilage removal step is about 9,000 rpm. In some embodiments, the maximum threshold rotational speed is about 8,000 rpm. In some embodiments, the maximum threshold rotational speed is about 7,000 rpm. In some embodiments, the maximum threshold rotational speed is about 6,000 rpm. In some embodiments, the maximum threshold rotational speed is about 5,000 rpm. In some embodiments, the maximum threshold rotational speed is about 4,000 rpm. In some embodiments, the maximum threshold rotational speed is about 3,000 rpm.

Figure 3A:
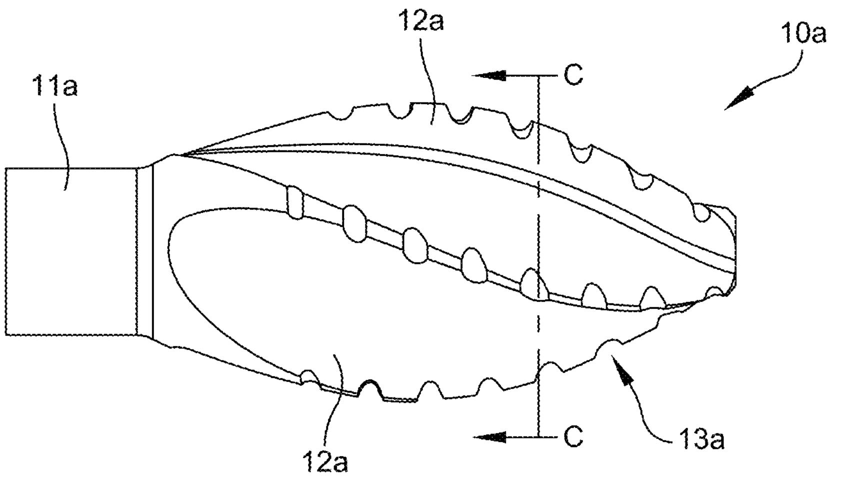
FIGS. 3A-3D are illustrations of some examples of surgical burrs for use in the preferential cartilage removal procedure of the present disclosure.

FIGS. 3A, 3B, 3C, and 3D are schematic illustrations of some examples of the burr used in the method of the present disclosure. FIG. 3A shows a burr 10*a* that is provided at the terminal end of a shaft 11*a*. As in any typical orthopedic burr, the shaft is configured to be attached to a hand-held driving tool that the operating surgeon can use to hold and manipulate the burr while the driving tool is rotating the burr at a desired speed. The burr 10*a* comprises a plurality of cutting flutes 12*a* that have a negative rake angle of about −30 degrees. The burr 10*a* is shaped so that the outline of the rotating burr 10*a* defined by the cutting flutes 12*a* has a bulbous shaped perimeter as shown.

Figure 3B:
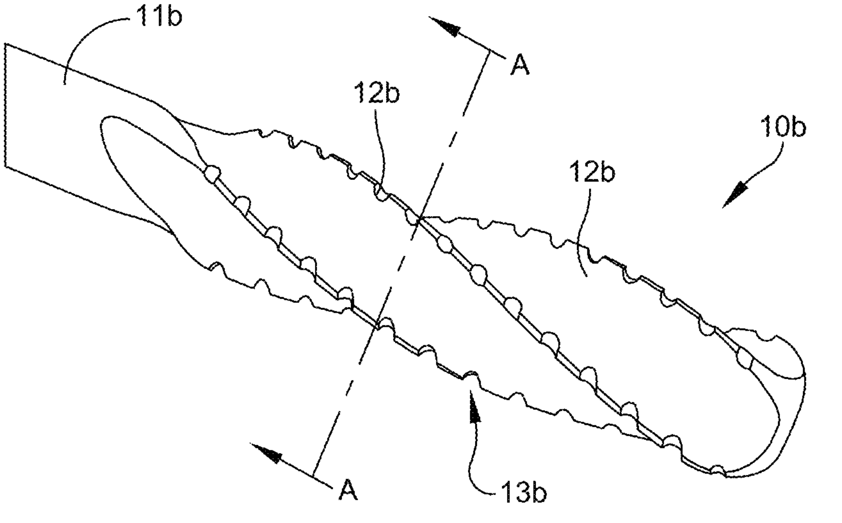

FIG. 3B shows a burr 10*b* according to another embodiment. The burr 10*b* is provided at the terminal end of a shaft 11*b* which is configured to be attached to a hand-held driving tool. The burr 10*b* also comprises a plurality of cutting flutes 12*b* that have a negative rake angle of about −30 degrees. The burr 10*b* is shaped so that the outline of the rotating burr 10*a* defined by the cutting flutes 12*b* has a straight perimeter similar to a cylinder.

Figure 3C:
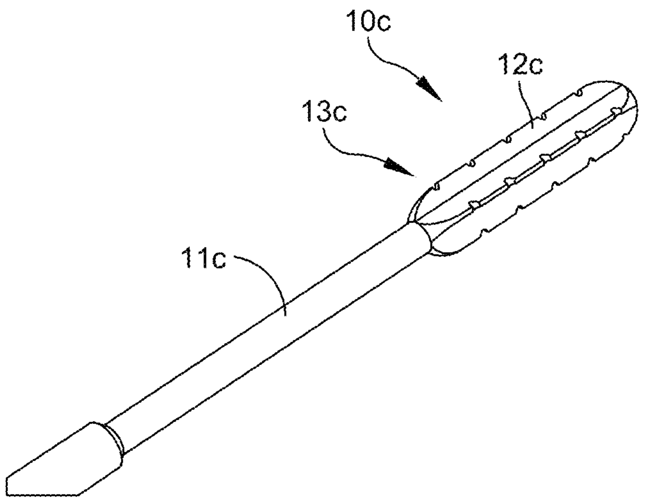

FIG. 3C shows a burr 10*c* according to another embodiment. The burr 10*c* is provided at the terminal end of a shaft 11*c* which is configured to be attached to a hand-held driving tool. The burr 10*c* also comprises a plurality of cutting flutes 12*c* that have a negative rake angle of about −30 degrees. The burr 10*c* is shaped so that the outline of the rotating burr 10*c* defined by the cutting flutes 12*c* has a straight perimeter.

Figure 3D:
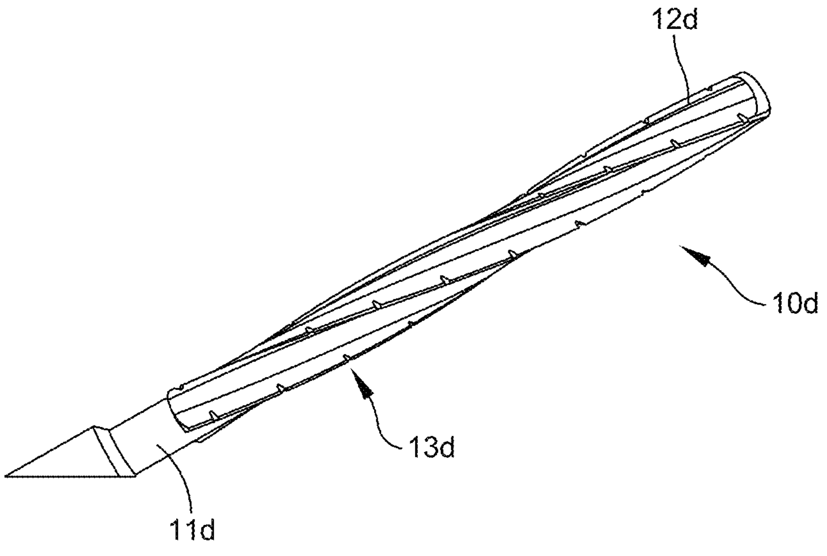

FIG. 3D shows a burr 10*d* according to another embodiment. The burr 10*d* is provided at the terminal end of a shaft 11*d* which is configured to be attached to a hand-held driving tool. The burr 10*d* also comprises a plurality of cutting flutes 12*d* that have a negative rake angle of about −30 degrees. The burr 10*d* is shaped so that the outline of the rotating burr 10*d* defined by the cutting flutes 12*d* has a straight perimeter.

In some embodiments, maneuvering the burr within the joint against the cartilage involves urging the rotating burr against the cartilage.

In some embodiments, the plurality of cutting flutes 12*a*, 12*b*, 12*c*, 12*d* on the burr 10*a*, 10*b*, 10*c*, 10*d* can have a negative rake angle within the range of values disclosed herein.

As shown in FIGS. 3A, 3B, and 3D, in some embodiments, the plurality of cutting flutes 12*a*, 12*b*, 12*d* are arranged in a helical configuration. As shown in FIG. 3C, in some embodiments, the plurality of cutting flutes 12*c* are arranged in a straight configuration.

Figure 4A:
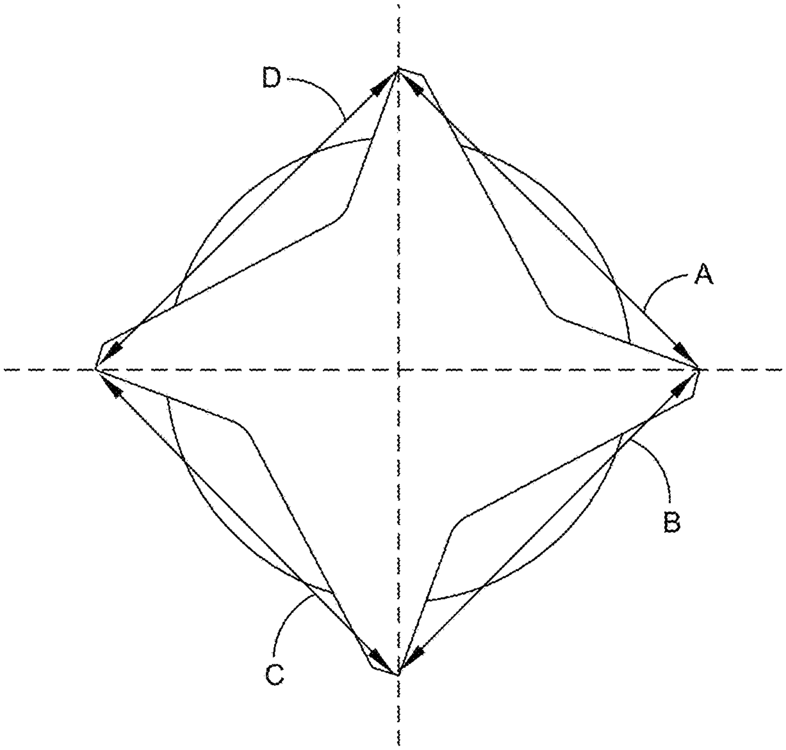
FIGS. 4A and 4B are cross-sectional illustrations of a burr showing different configurations with respect to tangential flute spacings of burrs.
Figure 4B:
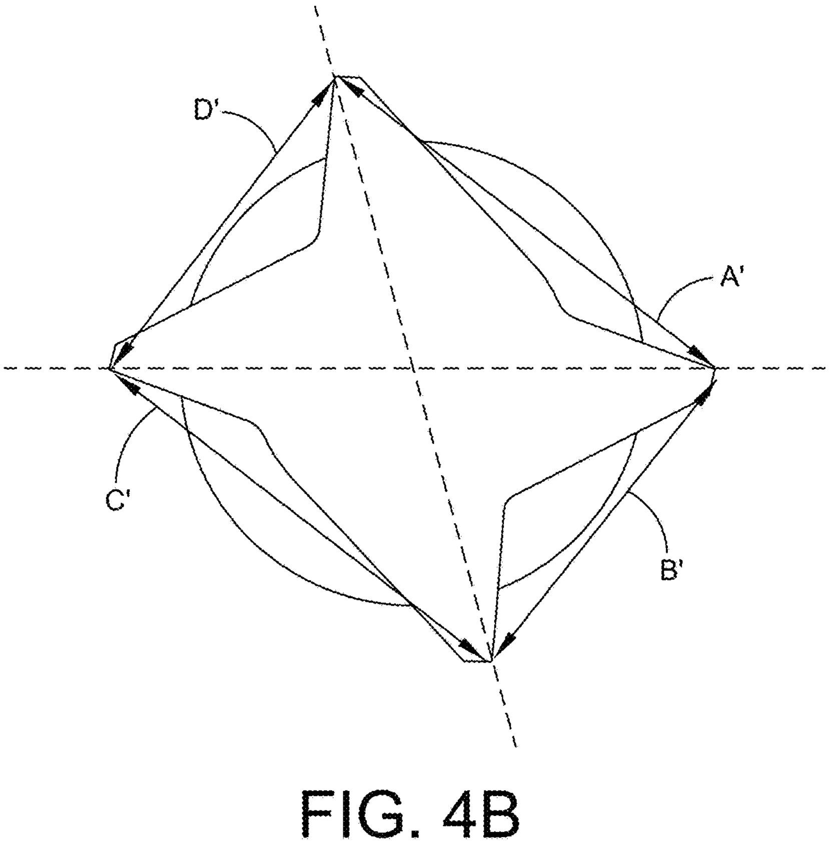

Referring to FIGS. 4A and 4B, in some embodiments, the plurality of cutting flutes can have constant tangential flute spacing or variable tangential flute spacing. FIG. 4A shows an embodiment where the tangential flute spacings A, B, C, and D are constant (i.e. the same). FIG. 4B shows an embodiment where the tangential flute spacings A', B', C', and D; are different.

Figure 5:
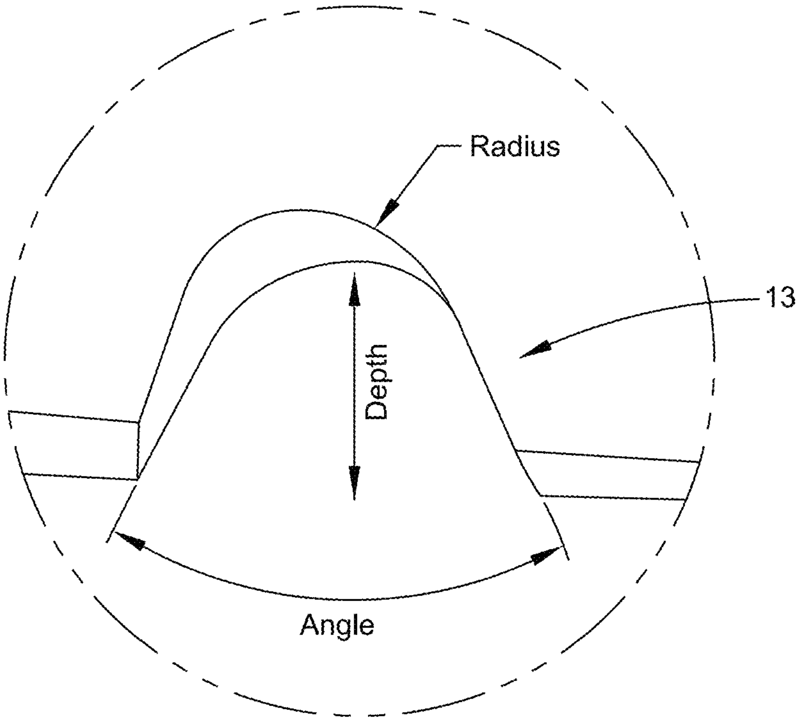
FIG. 5 is a detailed view of one example of a chip splitter on the cutting flutes of the burrs according to the present disclosure.

In some embodiments, each of the plurality of cutting flutes 12*a*, 12*b*, 12*c*, 12*d* comprise a plurality of chip splitters 13*a*, 13*b*, 13*c*, 13*d*. Chip splitters are known in the art to allow debris to pass through the cutting flutes during tissue removal procedures. The size and frequency of the chip splitters on their respective cutting flutes can be varied as desired. Referring to FIG. 5, a close-up detailed view of an exemplary chip splitter 13 is shown. The preferred size of the chip splitters for cartilage removal is: depth=0.008±0.004 inches; internal angle=45°±10°; radius at full depth=0.005 inches; and pitch=0.31±0.010 inches. Pitch refers to the axial distance from one chip splitter to the next, i.e. center-to-center distance.

By using a burr having the noted negative rake angle according to the method disclosed herein, the inventors have unexpectedly discovered that the combination of the defined negative rake angle of the burr's flutes and the particularly selected burr speed not greater than the defined maximum threshold enabled the operating surgeon to effectively remove the cartilage while only minimally, if at all, cutting into the harder subchondral bone. At a minimum, the beneficial characteristics afforded by the method of the present disclosure are: (1) a preferential cutting action by the burr that has a sweet spot cutting effectiveness wherein the burr, while effectively cuts into and removes cartilage, does not cut into subchondral bone but rather skids on the surface of the subchondral bone after the cartilage tissue is removed; and (2) providing a clear noticeable tactile feedback to the operating surgeon when the rotating burr contacts the subchondral bone. This tactile feedback alerts the surgeon to reduce applied cutting pressure so that any cutting of the subchondral bone is prevented or minimized. This effect allows the cartilage to be preferentially removed from the subchondral bone. Such helpful tactile feedback has not been observed by the surgeons performing cartilage removal procedures using conventional methods.

Experimental Data

A matched set of donor left and right foot specimen were used to compare the cartilage removal procedure of the present disclosure in removing cartilage from a joint against the conventional method of removing cartilage from a joint. The procedures were compared in removing cartilage from three different joints: TMT (tarsometatarsal) joint; first MTP (metatarsalophalangeal) joint; and CC (calcaneocuboid) joint. The operation sites were prepared by an experienced surgeons using a standard incision for joint preparation and arthrodesis. Then, a skilled surgeon performed the cartilage removal in the above-mentioned joints in the left and right foot specimen. In the right foot specimen, the surgeon used the conventional burr that has a positive rake angle of +17 degrees rotating at 6,000 rpm to remove cartilage in the TMT joint and used the preferential cartilage removal procedure disclosed herein (i.e., used the burr 10*a* shown in FIG. 2A with a negative rake angle of 30 degrees rotating at 6,000 rpm) to remove cartilage in the 1$^{st}$ MTP and CC joints. In the left foot specimen, the surgeon used the preferential cartilage removal procedure disclosed herein to remove cartilage in the TMT joint and used the conventional burr rotating at 6,000 rpm to remove cartilage in the 1$^{st}$ MTP and CC joints. To drive the burrs, NSK surgical system (Surgic Pro) was used to drive the burrs at a maximum setting of 6,000 rpm without irrigation.

During the cartilage removal procedures, the surgeon noted the ease or difficulties in judging the transition point when the cartilage removal was completed and undesired cutting of the subchondral bone began. After the completion of cartilage removal procedure, the joints were opened to visually check and evaluate the quality of the cartilage removal in the joints. The quality of cartilage removal were visually evaluated. The quality of cartilage removal refers to the degree in which the subchondral bone was unintentionally removed by the burr. The results of the experiment are summarized in Table 1 below:

TABLE 1

Summary of Test Results

| Joint operated on | Right Foot Specimen | | | Left Foot Specimen | | |
|---|---|---|---|---|---|---|
| | Burr Type used | Bone Cutting Observed | Cartilage Cutting Observed | Burr Type used | Bone Cutting Observed | Cartilage Cutting Observed |
| TMT | Standard osteotomy burr | Yes | Yes | Inventive burr | No | Yes |
| 1$^{st}$ MTP | Inventive burr | No | Yes | Standard osteotomy burr | Yes | Yes |
| CC | Inventive burr | No | Yes | Standard osteotomy burr | Yes | Yes |

Standard osteotomy burr had a rake angle of +17° and Inventive burr had a rake angle of −30°.

In all three joints tested, both burr types cut the cartilage. However, in the joints prepared with the conventional burr having a positive rake angle, noticeable amount of subchondral bone was cut and removed despite the skilled surgeon's best efforts to manually detect the cutting burr's transition between the osteochondral cartilage and subchondral bone. In other words, the tactile feedback of the burr was inadequate to signal the need to stop the cutting when bone was encountered during the de-cortication procedure. In contrast, in the joints prepared with the burr having a negative rake angle of 30 degrees as an example of an embodiment according to the present disclosure, no bone removal was observed when the joints were opened for visual inspection. Based on the experiences of surgeons in cartilage removal procedures in arthrodesis, the noticeably better preferential cartilage removal performance observed with the method of the present disclosure was unexpected.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

I claim:

1. A surgical burr for preferential removal of cartilage from a bone at a joint, the burr comprising:

a shaft having a proximal end suitable for operable attachment to a powered driver and a distal end; and a cutting head disposed at the distal end and having a maximum diameter of about 2 mm to about 4 mm, the cutting head including a plurality of cutting flutes extending axially along the cutting head, each cutting flute:

(i) defining a negative rake angle between about −10° and −50°; and (ii) (ii) carrying a plurality of chip splitters, each chip splitter having a depth of 0.008±0.004 inches, an internal angle of 45°±10°, a radius at full depth of 0.005 inches, and a pitch of 0.31±0.010 inches measured as an axial center-to-center distance between adjacent chip splitters.

2. The surgical burr of claim 1, wherein the plurality of cutting flutes are arranged in a helical configuration about the cutting head.

3. The surgical burr of claim 1, wherein the plurality of cutting flutes are arranged in a straight configuration.

4. The surgical burr of claim 1, wherein the plurality of cutting flutes have variable tangential flute spacing.

5. The surgical burr of claim 1, wherein the plurality of cutting flutes have equal tangential flute spacing.

6. The surgical burr of claim 1, wherein each of the negative rake angles is about −30°±5°.

7. The surgical burr of claim 1, wherein the cutting head has a bulbous outer profile with a maximum diameter located intermediate the proximal and the distal ends of the cutting head.

8. The surgical burr of claim 1, wherein the cutting head has a substantially cylindrical outer profile with a constant diameter along an axial length of the cutting head.

9. A surgical system for preferentially removing cartilage from a bone at a joint, the system comprising:

(a) the surgical burr of claim 1; and (b) a hand-held powered driver operatively connectable to the shaft and configured to rotate the surgical burr at a rotational speed limited to be at or below 10,000 revolutions per minute.

10. The system of claim 9, wherein the powered driver limits the rotational speed to not more than about 6,000 revolutions per minute.

11. The system of claim 9, wherein the powered driver is configured to provide selectable maximum rotational speeds of 6,000 rpm, 8,000 rpm, and 10,000 rpm.

12. The system of claim 9, wherein the powered driver is configured to deliver a torque sufficient to rotate the surgical burr at speeds between about 0.5 rpm and about 10,000 rpm.

* * * * *